(12) United States Patent
Lee et al.

(10) Patent No.: US 6,207,139 B1
(45) Date of Patent: Mar. 27, 2001

(54) ANTI-TARTAR DENTAL PRODUCT AND RELATED METHOD

(75) Inventors: G Jae Lee, Trumbull; Alexander George Ziemkiewicz, Shelton; David Robert Williams, Monroe; Stephen Roy Barrow, Trumbull, all of CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/395,064

(22) Filed: Sep. 13, 1999

Related U.S. Application Data

(60) Provisional application No. 60/129,779, filed on Apr. 16, 1999.

(51) Int. Cl.[7] ............................... A61K 7/16; A61K 7/18
(52) U.S. Cl. ................................ 424/52; 424/49; 424/57
(58) Field of Search ........................................... 424/49.58

(56) References Cited

U.S. PATENT DOCUMENTS

| | | | |
|---|---|---|---|
| 4,080,440 | 3/1978 | DiGiulio et al. | 424/49 |
| 4,183,915 | 1/1980 | Gaffar et al. | |
| 4,460,565 | 7/1984 | Weststrate et al. | |
| 4,885,155 | 12/1989 | Parran, Jr. et al. | |
| 4,891,211 * | 1/1990 | Winston | 424/52 |
| 5,037,639 | 8/1991 | Tung | |
| 5,135,548 * | 8/1992 | Golden et al. | 55/25 |
| 5,268,167 | 12/1993 | Tung | |
| 5,437,857 | 8/1995 | Tung | |
| 5,531,983 | 7/1996 | Van Velthuijsen | |
| 5,534,244 | 7/1996 | Tung | |
| 5,571,502 | 11/1996 | Winston et al. | |
| 5,599,527 | 2/1997 | Hsu et al. | |
| 5,603,922 | 2/1997 | Winston et al. | |
| 5,605,675 | 2/1997 | Usen et al. | |
| 5,614,175 | 3/1997 | Winston et al. | |
| 5,645,428 * | 7/1997 | Yarborough | 433/215 |
| 5,698,182 | 12/1997 | Prencipe et al. | |
| 5,713,738 * | 2/1998 | Yarborough | 433/215 |
| 5,833,957 | 11/1998 | Winston et al. | |
| 5,843,406 | 12/1998 | Mordarski et al. | |
| 5,855,871 | 1/1999 | Masters et al. | |
| 5,858,333 | 1/1999 | Winston et al. | |
| 5,866,102 | 2/1999 | Winston et al. | |
| 5,891,448 | 4/1999 | Chow et al. | |
| 5,895,641 | 4/1999 | Usen et al. | |

FOREIGN PATENT DOCUMENTS

| | | |
|---|---|---|
| 2 164 383 | 12/1971 | (DE) . |
| 1 408 922 | 10/1975 | (GB) . |
| 9143043 | 6/1997 | (JP) . |

OTHER PUBLICATIONS

Soap/Cosmetics/Chemical Specialties "Beyond Fluoride, The Enamelon Phenomenon"—p. 66, Jun. 1998.
http://www.enamelon.com/prof/pf/ss.htm Latest Clinical Data "Enamelon" ® (Jul. 8, 1999) Abstract from Enamelon Website Professionial.*
Hall et al Caries Res 32: 312, 1998.*
Kleber et al J. Dent. Res 77 (Spec ISS B)843, 1998.*
Tanzer et al.caries Res 31:288, 1997.*
Mundorf et al. J. Dent. Res. 77 (Spec. ISS. A): 246, 1990.*
Schemehorn et al J. Dent. Res 77 (Spec. ISS A):188, 1998.*
Schemehorn et al J. Dent. Res 76 (Spec. ISS):376, 1997.*
Tanzer et al J. Dent. Res. 76 (Spec. ISS:):134, 1997.*
Munoz et al J. Dent. Res. 77 (Spec. ISS. A):242, 1998.*
Yaskell et al J. Dent. Res. 77 (Spec. ISS. A):188, 1998.*
Wolinsky et al. J. Dent. Res. 77 (Spec. ISS. A):246, 1998.*
Kardos et al J. Dent. Res. 77 (Spec. ISS. A):246, 1998.*
Snagne–Asnero et al J. Dent. Res. 76 (Spec ISS):255, 1997.*
Rosenblum et al J. Dent. Res 76 (Spec. ISS.):17, 1997.*

* cited by examiner

Primary Examiner—Shep K. Rose
(74) Attorney, Agent, or Firm—Milton L. Honig

(57) ABSTRACT

An oral product and method is provided for inhibiting tartar formation on the teeth. The product is housed in a container and includes a first composition containing a water soluble calcium phosphate salt or monolithic combination of calcium and phosphate salts in a carrier with the first composition having a pH less than 7, and a second composition containing an alkaline material and a fluoride ion source in a carrier to achieve a pH greater than 7.5. The first and second compositions are separated from one another prior to use. When combined upon application to the teeth, the first and second compositions form a system for inhibiting tartar around the teeth.

19 Claims, No Drawings

ANTI-TARTAR DENTAL PRODUCT AND RELATED METHOD

This Application claims benefit of U.S. provisional 60/129,779 filed Apr. 16, 1999.

BACKGROUND OF THE INVENTION

1. Field of the Invention

The invention relates to new anti-tartar systems, dentifrice compositions containing these systems and their use in controlling tartar accumulation on teeth.

2. The Related Art

Tartar, known also as calculus, is a hard mineralized deposit which forms around teeth. This formation arises from deposition of crystals of calcium phosphate in the pellicle and the extracellular matrix of dental plaque. Various forms of calcium phosphate have been identified but the most difficult to remove and thermodynamically most stable form is called hydroxyapatite (HAP). Amorphous forms of calcium phosphate are believed to be the precursors of HAP. Regular brushing can usually remove the amorphous forms but is not fully effective to dislodge the final stable calculus form. Therefore it is desirable to prevent amorphous forms of calcium phosphate from transforming into HAP. The art has recognized that agents which interfere with the formation of HAP crystallization will be effective anti-tartar agents.

Soluble inorganic pyrophosphate salts have over the last decade set the commercial standard as tartar control agents. This technology has been reported by Parran, Jr. et al. in a series of patents including U.S. Pat. No. 4,590,077, U.S. Pat. No. 4,515,772 and U.S. Pat. No. 4,684,518.

Anionic polymers, especially carboxylate group functionalized polymers have been widely reported as effective against calculus. Commercially most significant has been the use of synthetic, linear anionic polymers of higher molecular weight in combination with the inorganic pyrophosphates. This technology derives from work done by Gaffar et al. reported in a series of patents including U.S. Pat. No. 4,627,977, U.S. Pat. No. 4,806,340, U.S. Pat. No. 4,806,342, U.S. Pat. No. 4,808,400 and U.S. Pat. No. 4,808,401. Anionic polymers described therein were found to inhibit the action of pyrophosphatase in the mouth and therefore allowing greater efficacy of the inorganic pyrophosphate. The commercially operative polymer is a methyl vinyl ether/maleic anhydride copolymer, available under the GAF trademark Gantrez.

Organic phosphonic acid derivatives, some in polymeric form, have been disclosed in U.S. Pat. No. 3,934,002 (Haefele). EP 0 341 662 (Amjad) cites a tartar inhibiting oral composition that includes a fluoride source, a dental abrasive, a carboxylate polymer and various phosphonic acids and their derivatives. A phosphated acrylic acid/hydroxyethyl methacrylate/alkyl methacrylic acid ester copolymer has been suggested in GB 2 139 635B (Causton) as useful in an oral composition for treating teeth.

Evident from the foregoing review of the art is the considerable effort expended to devise better tartar control compositions. By no means, however, has any of the reported art been able to more than attenuate the problem. There is considerable room for improvement over the known control agents.

Accordingly, it is an object of the present invention to provide a product of improved efficacy in controlling formation of tartar.

A still further object of the present invention is to provide a tartar control product of improved taste, safety and appearance.

These and other objects of the present invention will become more apparent in light of the detailed description and Examples which follow.

SUMMARY OF THE INVENTION

An anti-tartar dental product is provided comprising:
(i) a container;
(ii) an oral composition stored within the container, the composition including:
  (a) a first composition comprising from about 0.01 to about 30% by weight of a water-soluble calcium phosphate or monolithic combination of water soluble calcium and phosphate salts, the composition having a pH less than 7; and
  (b) a second composition including from about 0.01 to about 30% by weight of an alkaline material and an anti-caries effective amount of a fluoride ion source, the second composition having a pH greater than 7.5 and stored separately from the first composition in a manner to avoid contact between the phosphate and the alkaline material;
(iii) instructions printed on the container directing use of the composition to control tartar when applied to the teeth.

A method is provided for controlling dental tartar which includes:
(i) obtaining a product which includes:
  (a) a first composition comprising from about 0.01 to about 30% by weight of a water-soluble calcium phosphate or monolithic combination of water soluble calcium and phosphate salts, the composition having a pH less than 7; and
  (b) a second composition comprising from about 0.01 to about 30% by weight of an alkaline material and an anti-caries effective amount of a fluoride ion source, the second composition having a pH greater than 7.5 and stored separately from the first composition in a manner to avoid contact between the phosphate and the alkaline material;
(ii) extruding a portion of first and second compositions onto a toothbrush; and
(iii) brushing the teeth with the combination of first and second compositions.

DETAILED DESCRIPTION OF THE INVENTION

Products intended for remineralization of teeth ordinarily employ calcium and phosphate ions. Naturally there is great concern that these ions can be diverted from remineralization to calculus forming hydroxyapatite. Now it has been discovered that when a water soluble calcium phosphate salt is stored within one composition held at a low pH and mixed after storage with a second composition having a high pH, the result is a significant reduction in normal tartar formation against the teeth.

Separate storage of the two compositions of this invention may be accomplished through a dual compartment dispenser. U.S. Pat. No. 4,687,663 (Schaeffer) discloses a dual-compartment package respectively storing a peroxide gel and a bicarbonate paste. Pump packaging with multiple compartments is reported in U.S. Pat. No. 5,038,963 (Pettengill et al.) and U.S. Pat. No. 5,020,694 (Pettengill)

which are embodied in a U.S. product known as Mentadent® Baking Soda & Peroxide toothpaste.

Of course, delivery of compositions according to the present invention is not limited to unitary albeit multicompartmented dispensers nor to totally segregated compartments. The dispenser may be a system in the form of two individual tubes quite separate from one another but packaged within a kit. Ribbons of the dentifrice from each tube are delivered to a toothbrush with mixing of the compositions occurring in the mouth. Delivery may also be from a single chambered tube except that each of the two compositions are semi solid strips positioned side-by-side touching but not mixing with one another. The relatively high viscosity of the products prevents any substantial transference of either pH change or components between the two strips. Illustrative of this technology is a U.S. product sold by Colgate® under the Baking Soda & Peroxide brand. Still another method of delivery may be a single composition such as a paste or gel housing an alkaline environment. Monocalcium phosphate compositions may be dispersed throughout the alkaline composition yet separated from contact by a coating encapsulating the phosphate. Activation occurs in the mouth through the presence of water or saliva which penetrates the encapsulating coating releasing phosphate salt to interact with the alkaline environment.

A critical component of the first composition of this invention is a water soluble calcium phosphate salt. By the term "water soluble" is meant a solubility of at least 0.1 gram in 100 ml water at 25° C. Most preferred is monocalcium hydrogen phosphate but also of potential use are calcium polyol phosphates (e.g. calcium glycerophosphate) and monocalcium ammonium phosphate salts. Monolithic compositions of water soluble calcium and phosphate salts may be employed as alternatives to pre-formed water soluble calcium phosphates. By the term "monolithic" is meant separate water soluble calcium salts and phosphate salts which from solution may metathesize into calcium phosphates in solution or later upon mixing with the second composition. Illustrative calcium salts include the halides, sulphates, nitrates, citrates, sugars and $C_1$–$C_6$ carboxylates. Most preferred is calcium chloride, calcium sulphate and calcium acetate. The monolithic partner phosphate salts may be alkali, ammonium or combination salts thereof. Examples include sodium ammonium phosphate, sodium phosphate, ammonium phosphate and potassium phosphate. The watersoluble calcium phosphate salts or the monolithic calcium and phosphate salts (by weight of calcium and phosphate ions only) may be present in amounts ranging from 0.01 to 30%, preferably from 0.1 to 20%, optimally from 1 to 10% by weight of the first composition.

Solubility of the phosphate salt is maintained in the first composition by having an acidic environment. The pH will be less than 7, preferably from 1 to 6.5, more preferably from 1.8 to 6, optimally from 2.5 to 5.5.

The second composition of the present invention requires an alkaline material so that the second composition has a pH greater than 7, preferably from 7.2 to 11, more preferably from 8 to 10, optimally from 8.5 to 9.5. Alkaline materials suitable to achieve the pH are sodium bicarbonate, potassium bicarbonate, sodium carbonate, potassium carbonate, calcium carbonate, calcium oxide, sodium hydroxide, potassium hydroxide and mixtures thereof. Amounts of the alkaline material may range from 0.1 to 60%, preferably from 0.5 to 30%, more preferably from 1 to 20%, optimally from 3 to 15% by weight of the second composition.

Advantageously, compositions of this invention, especially the second composition may contain a fluoride anticaries compound. Illustrative of such fluoride compounds are sodium fluoride, potassium fluoride, calcium fluoride, magnesium fluoride, stannous fluoride, stannous monofluorophosphate, sodium monofluorophosphate and copper fluoride. Most preferred is sodium fluoride. These sources should release anywhere from about 25 to about 5,000 ppm of fluoride ion. The anti-caries compound will normally be present in an amount from about 0.01 to about 5%, preferably from 0.1 to 2.5%, optimally from 0.2 to 1.5% by weight of combined first and second compositions.

The compositions of the present invention may be in the form of either a toothpaste, gel, powder or mouthwash. Most preferably the compositions are either pastes or gels. Especially suitable is where the phosphate salt is incorporated in a gel and the alkaline material incorporated into a paste. These compositions may include water or be anhydrous.

The phosphate salt as well as the alkaline material will be delivered through a pharmaceutically acceptable carrier. The term "pharmaceutically acceptable carrier" will include such functional ingredients as water, humectants, abrasives, thickeners, surfactants and combinations thereof. Total levels of these materials may range anywhere from about 1 to about 99%, preferably from 20 to 80%, optimally from 30 to 60% by weight.

Acidity in the first composition may be achieved by formulating with a peroxide such as hydrogen peroxide, inorganic acids such as phosphoric, hydrochloric, nitric or boric acids, and organic $C_2$–$C_{20}$ carboxylic acids such as citric, malic, lactic, alginic, succinic, tartaric and ascorbic acids. Soluble salts may also be employed such as potassium bitartrate, sodium acid citrate, acid phosphate and pyrophosphate salts such as monosodium phosphate and disodium pyrophosphate. Levels of the acidity inducing substances may range in amounts from about 0.1 to about 20%, preferably from about 0.5 to about 10%, optimally from 1.0 to 8% by weight of the first composition. Hydrogen peroxide and phosphoric acid are the preferred substances.

Among the carriers, water when present may range in amounts from about 1 to 95%, preferably from 20 to 60%, optimally from 30 to 50% by weight of each of the compositions. Of course some formulations may be anhydrous.

Humectants are usually also present as one of the carriers. Illustrative of this category are sorbitol, maltitol, mannitol, glycerin and polyethylene glycols (e.g. Carbowax). Amounts of the humectant may range from 1 to 60%, preferably from about 5 to about 50%, optimally from 10 to 40% by weight of each composition.

Abrasives are normally present in toothpastes and some gels. These may include sodium metaphosphate, dicalcium phosphate (which is not considered a water-soluble phosphate), calcium pyrophosphate, silica, alumina, chalk, insoluble bicarbonate salts, and mixtures thereof. Amounts of the abrasives may range from about 1 to about 80%, preferably from 5 to 50% by weight of each composition.

Thickeners are a further type of carrier which can be included in the compositions of this invention. Illustrative thickeners such as sodium carboxy-methyl cellulose, hydroxy ethyl cellulose, methyl cellulose, ethyl cellulose, gum tragacanth, gum arabic, gum karaya, sodium alginate, carrageenan, guar, xanthan gum, Irish moss, starch, modified starch, Carbomers (crosslinked acrylates) and mixtures thereof. Inorganic substances may also be suitable, especially silica aerogels and magnesium aluminum silicate (e.g. Veegum). Amounts of the thickener may range from about 0.01 to about 30%, preferably from 0.1 to 20%, optimally from 0.5 to 15% by weight of a composition.

Surfactants are also considered to be within the carrier definition. Surfactants may either be anionic, nonionic, cationic or amphoteric. Most preferred are sodium lauryl sulphate, sodium dodecylbenzene sulphonate and sodium lauryl sarcosinate. Surfactants may be present in an amount from about 0.5 to about 10%, preferably from 0.8 to 5% by weight of a composition.

Gel compositions are structured with substances than can be characterized as either humectants or surfactants. For instance, a typical gel structurant is a polyoxyethylene-polyoxypropylene copolymer such as those sold by the BASF Corporation under the trademark Pluronic® F88, F99, F108 and F127. These materials are also known as Poloxamers and employed in amounts from about 5 to about 30%, preferably between about 18 and about 25% by weight of a composition.

Flavors may also be present in the compositions. These flavors may be based on oils of spearmint and peppermint. Examples of other flavoring materials include menthol, clove, wintergreen, eucalyptus and aniseed. Flavors may range in concentration from about 0.1 to about 5% by weight of a composition.

Sweetening agents may also be included such as saccharin, sodium cyclamate, aspartame, ace-sulfame, xylitol and combinations thereof at levels from 0.1 to 10% by weight of a composition.

Gel compositions incorporating hydrogen peroxide may include a sequestering agent(s) such as a pyrophosphate or other phosphate for chelation of ferric/ferrous ion as well as other transition metal ions to enhance hydrogen peroxide stability. The sequestering agents may also be included within the paste compositions and are present in amounts from about 0.01 to about 20% by weight of a composition. Most preferred chelatants are tetrasodium pyrophosphate, sodium tripolyphosphate and sodium hexametaphosphate, all known to be effective at lower pH with little affinity for calcium ion. Other organic chelating agents such as sodium citrate and zinc citrate are also useful.

Other additives may also be incorporated such as preservatives, silicones, other synthetic or natural polymers such as Gantrez S97®, additional anti-tartar actives and antigingivitis actives. Among the additional anti-tartar agents are included zinc citrate, tetrasodium pyrophosphate, disodium pyrophosphate, dipotassium pyrophosphate, tetrapotassium pyrophosphate and mixtures thereof. Antigingivitis actives may include thymol, Triclosan, stannous gluconate and mixtures thereof. Amounts of each of the aforementioned ingredients will depend upon their function. Generally each of these substances will range in amounts from about 0.01 to about 20% by weight of a composition.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight of either the first or second composition unless otherwise indicated.

EXAMPLE 1

Typical of the present invention is a first composition in the form of a gel and a second composition in the form of a paste. Each of these formulations is held in a separate compartment of a dual-compartment dispenser similar to that disclosed in U.S. Pat. No. 5,038,963 (Pettengill et al.).

| Gel Composition 1A | |
|---|---|
| INGREDIENT | WEIGHT % |
| Glycerin | 40.00 |
| Pluronic F-127 | 20.00 |
| Monocalcium Phosphate Monohydrate | 1.60 |
| Hydrogen Peroxide (35% Active) | 4.285 |
| Phosphoric Acid | 0.40 |
| FD&C Blue No. 1 | 0.01 |
| Water | Balance |

| Paste Composition 1B | |
|---|---|
| INGREDIENT | WEIGHT % |
| Polyol II (70% Sorbitol) | 47.00 |
| Syloid 63XX (Hydrated Silica) | 15.00 |
| Sodium Bicarbonate | 10.00 |
| Sylox 15X | 6.00 |
| Polyethylene Glycol 1450 (PEG-32) | 5.00 |
| Ethyl Alcohol 38B | 2.84 |
| Sodium Lauryl Sulphate | 2.98 |
| Flavor | 1.10 |
| Cellulose Gum | 0.80 |
| Sodium Saccharin | 0.54 |
| Menthol | 0.50 |
| Sodium Fluoride | 0.44 |
| Titanium Dioxide | 0.30 |
| Water | Balance |

EXAMPLE 2

Another system typical of the present invention is a two part toothpaste. Each part is placed in a dual-compartment dispenser similar to that of Example 1.

| COMPONENTS | PASTE 2A (% WEIGHT) | PASTE 2B (% WEIGHT) |
|---|---|---|
| Sorbitol (70% Active) | 28.50 | — |
| Syloid 63XX (Hydrated Silica) | 20.00 | 18.0 |
| Glycerin | 28.00 | 32.0 |
| Monocalcium Phosphate | 6.49 | — |
| Citric Acid | 5.00 | — |
| Syloid 244 (Thickening Silica) | 3.00 | 0.5 |
| Xanthan Gum | 0.50 | — |
| Sodium Fluoride | — | 0.44 |
| FD&C Blue No. 1 | 0.01 | — |
| Sodium Bicarbonate | — | 25.0 |
| Sodium Lauryl Sulphate | — | 1.5 |
| Sodium Carboxymethyl Cellulose | — | 0.8 |
| Flavor | — | 1.0 |
| Titanium Dioxide | — | 0.4 |
| Sodium Saccharin | — | 0.2 |
| Water | balance | balance |

The pH of Paste 2A is approximately 2.0. Paste 2B has a pH of approximately 9.0. Strips of each of these are extruded onto a toothbrush. These strips are then brushed against the teeth thereby mixing them together.

EXAMPLE 3

Yet another system typical of the present invention is a two part toothpaste as described below. Each part is placed in a dual-compartment dispenser similar to that of Example 1.

| COMPONENTS | PASTE 3A (% WEIGHT) | PASTE 3B (% WEIGHT) |
|---|---|---|
| Sorbitol (70% Active) | 30.50 | — |
| Alumina | 20.00 | 18.0 |
| Polyol II | 10.00 | 32.0 |
| Malic Acid | 5.00 | — |
| Monocalcium Phosphate | 4.50 | — |
| Syloid 244 (Thickening Silica) | 3.00 | 0.5 |
| Xanthan Gum | 0.50 | — |
| Sodium Fluoride | — | 0.44 |
| FD&C Blue No. 1 | 0.01 | — |
| Sodium Bicarbonate | — | 25.0 |
| Sodium Lauryl Sulphate | — | 1.5 |
| Sodium Carboxymethyl Cellulose | — | 0.8 |
| Flavor | — | 1.0 |
| Sodium Carbonate | — | 0.4 |
| Sodium Saccharin | — | 0.2 |
| Water | balance | balance |

The pH of Paste 3A and 3B respectively are approximately 2 and 9. Strips of each of these pastes are placed onto a toothbrush. These strips are then brushed against the teeth thereby mixing them together.

EXAMPLE 4

This Example illustrates use of a monolithic calcium and phosphate salt combination to deliver the water soluble monocalcium phosphate component. Separate gel and paste formulations representing the first and second compositions of this invention were prepared with the following compositions.

Gel Composition 4A

| INGREDIENT | WEIGHT % |
|---|---|
| Glycerin | 40.00 |
| Pluronic F-127 ® | 20.00 |
| Hydrogen Peroxide (35% Active) | 4.29 |
| Calcium Chloride Dihydrate | 2.10 |
| Dibasic Sodium Phosphate | 1.00 |
| Phosphoric Acid (85% Active) | 1.50 |
| Sodium Citrate | 0.53 |
| FD&C Blue No. 1 | 0.01 |
| Water | Balance |

Paste Composition 4B

| INGREDIENT | WEIGHT % |
|---|---|
| Polyol II (70% Sorbitol) | 40.50 |
| Syloid 63XX (Hydrated Silica) | 15.00 |
| Sodium Bicarbonate | 10.00 |
| Sylox 15X | 6.00 |
| Polyethylene Glycol 1450 (PEG-32) | 3.00 |
| Ethyl Alcohol 38B | 2.84 |
| Sodium Lauryl Sulphate | 2.98 |
| Flavor | 1.10 |
| Cellulose Gum | 0.80 |
| Sodium Saccharin | 0.54 |
| Menthol | 0.50 |
| Sodium Fluoride | 0.44 |
| Titanium Dioxide | 0.30 |
| Water | Balance |

EXAMPLE 5

Yet another system typical of the present invention is a two part toothpaste as described below. Each part is placed in a dual compartment dispenser similar to that of Example 1.

Gel Composition 5A

| INGREDIENT | WEIGHT % |
|---|---|
| Glycerin | 40.00 |
| Pluronic F-127 | 20.00 |
| Monocalcium Phosphate Monohydrate | 3.10 |
| Phosphoric Acid (85% Active) | 0.85 |
| Water | Balance |

Paste Composition 5B

| INGREDIENT | WEIGHT % |
|---|---|
| Polyol II (70% Sorbitol) | 46.68 |
| Syloid 63XX (Hydrated Silica) | 15.00 |
| Sodium Carbonate | 6.50 |
| Sylox 15X (Hydrated Silica) | 6.00 |
| Polyethylene Glycol 1450 (PEG 32) | 5.00 |
| Ethyl Alcohol 38B | 2.84 |
| Sodium Lauryl Sulphate | 2.98 |
| Flavor | 1.00 |
| Cellulose Gum | 0.80 |
| Sodium Saccharin | 0.50 |
| Menthol | 0.50 |
| Sodium fluoride | 0.44 |
| Titanium Dioxide | 0.30 |
| Water | Balance |

The pH of 5A and 5B respectively are approximately 2.7 and 9.5

EXAMPLE 6

This Example illustrates use of monocalcium phosphate in a Gel composition along with Triclosan solubilized in alcohol.

Gel Composition 6A

| INGREDIENT | WEIGHT % |
|---|---|
| Glycerin | 40.00 |
| Pluronic F-127 | 20.00 |
| Alcohol SDA 38B | 5.00 |
| Monocalcium Phosphate, Monohydrate | 1.55 |
| Phosphoric Acid (95% Active) | 0.45 |
| Hydrogen Peroxide (35% Active) | 4.29 |
| Irgacare ® MP (Triclosan) | 0.67 |
| Water | Balance |

Paste Composition 6B

| INGREDIENT | WEIGHT % |
|---|---|
| Polyol II (70% Sorbitol) | 46.68 |
| Syloid 63XX (Hydrated Silica) | 15.00 |
| Sodium Bicarbonate | 10.00 |
| Sylox 15X (Hydrated Silica) | 6.00 |
| Polyethylene Glycol 1450 (PEG 32) | 3.00 |

-continued

| Paste Composition 6B | |
|---|---|
| INGREDIENT | WEIGHT % |
| Ethyl Alcohol 38B | 2.84 |
| Sodium Lauryl Sulphate | 2.98 |
| Flavor | 1.10 |
| Cellulose Gum | 0.80 |
| Sodium Saccharin | 0.54 |
| Menthol | 0.50 |
| Sodium Fluoride | 0.44 |
| Titanium Dioxide | 0.30 |
| Water | Balance |

The pH of 6A and 6B respectively are approximately 2.7 and 9.2

EXAMPLE 7

Another Example is shown using monocalcium phosphate in a Gel composition. Here Triclosan is incorporated into a Paste composition of elevated pH for eventual combination with the Gel.

| Gel Composition 7A | |
|---|---|
| INGREDIENT | WEIGHT % |
| Glycerin | 40.00 |
| Pluronic F-127 | 20.00 |
| Hydrogen Peroxide (35% Active) | 4.29 |
| Monocalcium Phosphate, Monohydrate | 3.10 |
| Phosphoric Acid (95% Active) | 0.85 |
| Water | Balance |

| Paste Composition 7B | |
|---|---|
| INGREDIENT | WEIGHT % |
| Polyol II | 44.93 |
| Syloid 63XX (Hydrated Silica) | 30.00 |
| Sodium Carbonate | 7.00 |
| Sylox 15X (hydrated Silica) | 2.00 |
| Ethyl Alcohol 38B | 2.84 |
| Sodium Lauryl Sulphate | 2.98 |
| Flavor | 1.30 |
| Irgacare ® MP (Triclosan) | 0.55 |
| Sodium Saccharin | 0.54 |
| Cellulose Gum | 0.80 |
| Menthol | 0.50 |
| Sodium fluoride | 0.44 |
| Titanium Dioxide | 0.30 |
| Water | Balance |

The pH of 7A and 7B respectively are approximately 2.7 and 9.2

EXAMPLE 8

A clinical trial was conducted to compare the dental product of Example 1 with an identical product that did not include monocalium phosphate monohydrate. The commercial toothpastes Aim® and Colgate Total® were used as reference samples, the latter product being a formulation containing triclosan.

Protocol for the clinical was as follows. Panelists were carefully selected to meet a long list of criteria such as exhibiting visible tartar within only 1 to 2 months of a professional cleaning. Tartar present on the lingual aspect of the 6 anterior Mandibular teeth was evaluated according to the Volpe/Manhold Scoring Index. Following an initial tartar assessment, each panelist received a thorough dental cleaning. Panelists were then given Aim® toothpaste for use over the following 3 weeks to allow tartar to build. Another tartar evaluation identified the baseline for a panelist's normal tartar growth rate. A second dental prophylaxis was then performed to remove dental tartar rendering the panelists ready to receive the first test product (Example 1 with monocalcium phosphate monohydrate). Tartar evaluations were then conducted after 2 and 3 weeks of product usage. Aim® was then given to the panelists for a 4 week washout period.

The Mandibular Anterior teeth were then scaled to remove tartar buildup over the washout period. Panelists were next assigned to use Colgate Total® for the subsequent 3 weeks. Evaluations were again conducted after the 2 and 3 week usage period. In a further phase of the test, the panelists were directed to use Aim® for another 4 week washout. Again, the Mandibular Anterior teeth were scaled to remove tartar buildup over the 4 week washout period. Panelists were then assigned to Example 1 where monocalcium phosphate monohydrate was absent (replaced by 2% zinc citrate) for the next 3 weeks. Tartar evaluations were conducted at the 2 and 3 week interval. Results of the tests are reported in the Table below.

TABLE I

CALCULUS CLINICAL

| | % CALCULUS REDUCTION AFTER 6 WEEKS |
|---|---|
| Aim °0 | +5 |
| Colgate Total ® | −30 |
| Example 1 (Calcium Phosphate) | −42 |
| Example 1 (Without Calcium Phosphate) | −24 |

Positive values indicate an increase in calculus. Negative values indicate a reduction. Table I reveals that Example 1 containing calcium phosphate had significantly better calculus inhibition performance than Aim®. The better performance is attributed to calcium phosphate which when absent from Example 1 allowed considerable more calculus formation.

EXAMPLE 9

A further study was conducted under a protocol similar to that described in Example 8 and utilizing some of the earlier data. All three cells of the test employed the same paste (sodium bicarbonate) composition as outlined below.

| Paste Composition 9A | |
|---|---|
| INGREDIENT | WEIGHT % |
| Polyol II (70% Sorbitol) | 33.30 |
| Syloid 63XX (Hydrated Silica) | 30.00 |
| Sodium Bicarbonate | 10.00 |
| Sylox 15X | 2.00 |
| Polyethylene Glycol 1450 (PEG 32) | 5.00 |
| Sodium Lauryl Sulphate | 2.98 |
| Alcohol 38B | 2.84 |
| Flavor | 1.30 |
| Cellulose Gum | 0.80 |
| Saccharin | 0.54 |
| Menthol | 0.50 |

-continued

Paste Composition 9A

| INGREDIENT | WEIGHT % |
|---|---|
| Sodium Fluoride | 0.44 |
| Titanium Dioxide | 0.30 |
| Water | Balance |

The gel compositions (containing monocalcium phosphate monohydrate) were different for each of the test cells. The formulations are reported in the Tables below.

Gel Composition 9B–9D

| | WEIGHT % | | |
|---|---|---|---|
| COMPOSITION | 9B | 9C | 9D |
| Glycerin | 40.00 | 39.00 | 39.00 |
| Pluronic F-127 | 20.00 | 21.00 | 21.00 |
| Hydrogen Peroxide (35% Active) | 4.285 | 4.285 | 4.285 |
| Monocalcium Phosphate Monohydrate | — | 1.07 | — |
| Disodium Phosphate | — | 0.20 | — |
| Methyl Salicylate | 0.50 | 0.50 | 0.50 |
| Calcium Chloride | — | — | 0.92 |
| Phosphoric Acid (95% Active) | 0.15 | 0.70 | 0.25 |
| Colorant | 0.005 | 0.01 | 0.01 |
| Water | Balance | Balance | Balance |

Table II provides the calculus reduction % results.

TABLE II

Calculus Reduction Results

| TEST FORMULATION | CALCIUM/PHOSPHATE (ppm) | % CALCULUS REDUCTION |
|---|---|---|
| 9A–B | 0.0/3877 | −24 |
| 9A–C | 810/8000 | −44 |
| 9A–D | 1250/1380 | −40 |

The study reveals that calcium is essential for a reduction in calculus. Levels of 810 and 1250 ppm calcium in combination with phosphate were sufficient to provide significant calculus reduction.

The foregoing description and examples illustrate selected embodiments of the present invention. In light thereof variations and modifications will be suggested to one skilled in the art, all of which are within the spirit and purview of this invention.

What is claimed is:

1. An anti-tartar dental product comprising:
   (i) a container;
   (ii) an oral composition stored within the container, the composition comprising:
      (a) a first composition comprising from about 0.1 to about 20% by weight of a peroxide and from about 0.01 to about 30% by weight of a water-soluble calcium phosphate or monolithic combination of water soluble calcium and phosphate salts, the composition having a pH less than 7; and
      (b) a second composition including from about 0.01 to about 30% by weight of an alkaline material and an anti-caries effective amount of a fluoride ion source, the second composition having a pH greater than 7.5 and stored separately from the first composition in a manner to avoid contact between the phosphate and the alkaline material.

2. The product according to claim 1 wherein the water-soluble phosphate salt is monocalcium hydrogen phosphate.

3. The product according to claim 1 wherein the alkaline material is selected from the group consisting of sodium bicarbonate, potassium bicarbonate, sodium hydroxide, potassium hydroxide, sodium carbonate, potassium carbonate, calcium carbonate, calcium oxide and mixtures thereof.

4. The product according to claim 1 wherein the pH of the first composition ranges from 2.5 to 5.5.

5. The product according to claim 1 wherein the pH of the second composition ranges from 7.2 to 11.

6. The product according to claim 1 wherein the pH of the first composition results from inclusion of a compound selected from the group consisting of hydrogen peroxide, inorganic acids, $C_2$–$C_{20}$ carboxylic acids and mixtures thereof.

7. The product according to claim 1 wherein the monolithic combination of water soluble calcium salts are selected from the group consisting of calcium chloride, calcium sulphate and calcium acetate and the respective phosphate salts are selected from the group consisting of sodium phosphate, ammonium phosphate and sodium ammonium phosphate.

8. The product according to claim 1 further comprising from about 0.01 to about 20% by weight of triclosan.

9. The product according to claim 1 further comprising from about 0.01 to about 20% by weight of a zinc salt.

10. The product according to claim 1 further comprising from about 0.01 to about 5% by weight of a fluoride compound.

11. A method for controlling dental tartar comprising:
   (i) obtaining a product which comprises:
      (a) a first composition comprising from about 0.1 to about 20% by weight of a peroxide and from about 0.01 to about 30% by weight of a water-soluble calcium phosphate or monolithic combination of water soluble calcium and phosphate salts, the composition having a pH less than 7; and
      (b) a second composition comprising from about 0.01 to about 30% by weight of an alkaline material and an anti-caries effective amount of a fluoride ion source, the second composition having a pH greater than 7.5 and stored separately from the first composition in a manner to avoid contact between the phosphate and the alkaline material;
   (ii) extruding a portion of first and second compositions onto a toothbrush; and
   (iii) brushing the teeth with the combination of first and second compositions.

12. The method according to claim 11 wherein the water-soluble phosphate salt is monocalcium hydrogen phosphate.

13. The method according to claim 11 wherein the alkaline material is selected from the group consisting of sodium bicarbonate, potassium bicarbonate, sodium hydroxide, potassium hydroxide, sodium carbonate, potassium carbonate, calcium carbonate, calcium oxide and mixtures thereof.

14. The method according to claim 10 wherein the pH of the first composition ranges from 2.5 to 5.5.

15. The method according to claim 10 wherein the pH of the second composition ranges from 7.2 to 11.

16. The method according to claim 11 wherein the pH of the first composition results from inclusion of a compound selected from the group consisting of hydrogen peroxide, inorganic acids, $C_2$–$C_{20}$ carboxylic adds and mixtures thereof.

17. The method according to claim 11 wherein the monolithic combination of water soluble calcium salts are selected from the group consisting of calcium chloride, calcium citrate, calcium sulphate and calcium acetate and the respective phosphate salts are selected from the group consisting of sodium phosphate, ammonium phosphate and sodium ammonium phosphate.

18. The method according to claim 11 further comprising from about 0.01 to about 20% by weight of triclosan.

19. The method according to claim 11 further comprising from about 0.01 to about 20% by weight of a zinc salt.

* * * * *